(12) United States Patent
Barzaghi et al.

(10) Patent No.: US 7,030,160 B2
(45) Date of Patent: Apr. 18, 2006

(54) PROPANOLAMINOTETRALINES, PREPARATION THEREOF AND COMPOSITIONS CONTAINING SAME

(75) Inventors: Laura Barzaghi, Monza (IT); Philippe R. Bovy, Mareil Marly (FR); Roberto Cecchi, Lodi (IT); Tiziano Croci, Milan (IT); Stefano Romagnano, Buccinasco (IT)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/297,291

(22) PCT Filed: May 29, 2001

(86) PCT No.: PCT/FR01/01652

§ 371 (c)(1),
(2), (4) Date: Aug. 8, 2003

(87) PCT Pub. No.: WO01/94307

PCT Pub. Date: Dec. 13, 2001

(65) Prior Publication Data

US 2004/0034070 A1 Feb. 19, 2004

(30) Foreign Application Priority Data

Jun. 6, 2000 (FR) .................................. 00 07190

(51) Int. Cl.
*A61K 31/216* (2006.01)
*C07C 311/08* (2006.01)

(52) U.S. Cl. ............ 514/567; 514/466; 514/524; 514/539; 514/605; 514/620; 514/648; 514/650; 514/652; 560/36; 560/37; 562/441; 562/451; 564/99; 564/165; 564/321; 564/337; 564/349; 564/350; 564/351

(58) Field of Classification Search ................ 514/466, 514/524, 539, 567, 605, 620, 648, 650, 652; 560/36, 37; 562/441, 451; 564/99, 165, 564/321, 337, 349, 350, 351
See application file for complete search history.

(56) References Cited

U.S. PATENT DOCUMENTS

| | | | | |
|---|---|---|---|---|
| 5,254,595 A | * | 10/1993 | Guzzi et al. | 514/652 |
| 5,723,489 A | * | 3/1998 | Sher et al. | 514/466 |
| 6,344,474 B1 | * | 2/2002 | Maruani et al. | 514/406 |
| 6,391,915 B1 | * | 5/2002 | Taniguchi et al. | 514/510 |

FOREIGN PATENT DOCUMENTS

| | | |
|---|---|---|
| EP | 0714883 | 6/1996 |
| EP | 0882704 | 12/1998 |
| EP | 0976720 | 2/2000 |

OTHER PUBLICATIONS

Kitasawa et al. "preparation of carbamoylphenyl . . . " CA 128:88683 (1998).*
Lendaris et al. "Reach through claims . . . " Intellectual property update, vol. 4, No. 5 (2004).*
Baker Botts "In print reachthrough claims" Attorney's practice profile news and event (2002).*

* cited by examiner

*Primary Examiner*—Celia Chang
(74) *Attorney, Agent, or Firm*—Jiang Lin

(57) ABSTRACT

The invention relates to phenoxypropanolamines, to pharmaceutical compositions containing them, to processes for preparing them, and to the method of use thereof in the treatment of diseases that are improved by beta-3 agonist action.

20 Claims, No Drawings

PROPANOLAMINOTETRALINES, PREPARATION THEREOF AND COMPOSITIONS CONTAINING SAME

The present invention relates to novel phenoxypropanolamines, to pharmaceutical compositions containing them, to a process for their preparation and to intermediates in said process.

International patent application WO-A-99/51564 describes propanolamine derivatives with general formula:

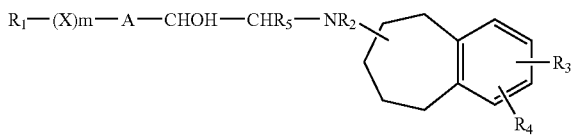

in which $R_1$ is an aryl, a heterocycle or a cycloalkyl, these compounds having an agonist activity as regards beta-3 adrenergic receptors and being capable of being used in treating a number of disorders such as ulcers, pancreatitis, obesity, urinary incontinence and pollakiuria.

European patent EP-A-0 375 560 describes aryloxypropanolaminotetralins that also have an activity as regards beta-3 adrenergic receptors but exercise an antagonist effect on these receptors.

It has now been discovered that certain phenoxypropanolaminotetralins with a structure close to that of compounds described in EP-A-0 375 560 have an agonist activity as regards beta-3 adrenergic receptors.

In one aspect, the present invention thus concerns phenoxypropanolamines with formula (I):

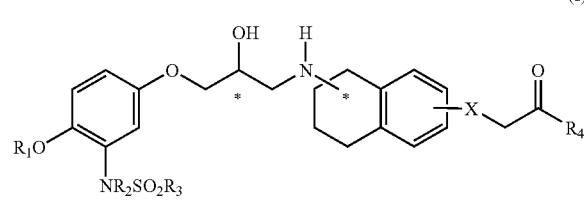

in which:
- $R_1$ and $R_2$ independently represent a hydrogen atom, a benzyl group, a benzoyl group, a —CO($C_1$–$C_4$)Alk group, a —$CH_2OCH_3$ group, a —COO($C_1$–$C_4$)Alk group or a benzyloxycarbonyl group; or
- $R_1$ and $R_2$ together form a carbonyl, methylene or di($C_1$–$C_4$) Alk-methylene group to constitute a heterocyclic structure together with the oxygen and nitrogen atoms carrying them;
- $R_3$ represents a hydrogen atom or a ($C_1$–$C_4$)Alk group;
- $R_4$ represents a hydroxyl group, a ($C_1$–$C_4$)alkoxy group or an —$NR_5R_6$ group;
- $R_5$ and $R_6$ independently represent a hydrogen atom; a ($C_1$–$C_4$)Alk group; an aryl or heteroaryl group optionally substituted with an $R_7$ group; an aralkyl or heteroaralkyl group optionally substituted with an $R_7$ group; or $R_5$ and $R_6$, together with the nitrogen atom carrying them, form a saturated or unsaturated 5 to 7 atom cycle;
- $R_7$ represents a hydrogen atom or a halogen atom, a hydroxyl group, a ($C_1$–$C_4$)Alk group, a ($C_1$–$C_4$)alkoxy group, a —COOH group, a —COO($C_1$–$C_4$)Alk group, a —CN group, an —NH($C_1$–$C_4$)Alk group or an —N($C_1$–$C_4$)$Alk_2$ group;
- X represents O or $CH_2$;

and their salts or solvates.

In the present description, the term "($C_1$–$C_4$)Alk" designates a monovalent radical of a saturated linear or branched chain $C_1$–$C_4$ hydrocarbon.

In the present description, the term "halogen" designates an atom selected from chlorine, bromine, iodine and fluorine.

"Aryl or heteroaryl groups" include in particular phenyl, naphthyl and pyridyl groups.

"Aralkyl or heteroaralkyl groups" include in particular benzyl, naphthylmethyl and pyridylmethyl groups.

"Saturated or unsaturated 5 to 7 atom cycles" include in particular pyrrolidine, piperidine, morpholine and thiomorpholine.

A preferred —COO($C_1$–$C_4$)Alk group is tert-butoxycarbonyl (Boc).

Preferred compounds include compounds in which the substituent —X—$CH_2$—CO—$R_4$ is attached to the 7 position of the tetralin.

Preferred compounds include compounds in which $R_3$ represents the ($C_1$–$C_4$)Alk group.

Salts of compounds with formula (I) in accordance with the present invention include addition salts with pharmaceutically acceptable mineral or organic acids such as the hydrochloride, hydrobromide, sulfate, bisulfate, dihydrogenphosphate, citrate, maleate, tartrate, fumarate, gluconate, methanesulfonate, 2-naphthalenesulfonate, etc., as well as addition salts that enable appropriate separation or crystallization of compounds with formula (I), such as the picrate or oxalate, or addition salts with optically active acids, for example camphosulfonic acids and mandelic acids or substituted mandelic acids.

Further, when compounds with formula (I) contain a free carboxy group, the salts also include salts with mineral bases, preferably those with alkali metals such as sodium or potassium, or with organic bases.

Optically pure stereoisomers and mixtures of isomers of compounds with formula (I) due to asymmetric carbon atoms in any proportion are also encompassed by the present invention.

Preferred compounds with formula (I) are compounds in which the configuration of the carbon carrying the OH group in the propanolamine is (S).

Other preferred compounds with formula (I) are compounds in which the configuration of the carbon bonded to the amino group in the tetralin is (S).

Particularly preferred compounds with formula (I) are compounds in which the configuration of the carbon atoms shown with an asterisk "*" is (S).

Other preferred compounds are compounds in which the tetralin is attached to the amino group in the beta position.

Compounds with formula (I) can be prepared by treating a compound with formula (II):

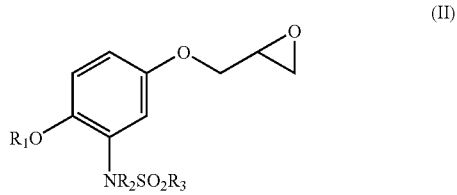

in which $R_1$, $R_2$ and $R_3$ are as indicated above, with an amine with formula (III):

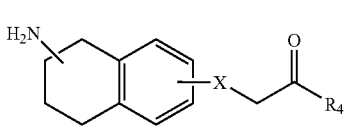

(III)

in which X and $R_4$ are as defined above, and optionally by transforming the compound with formula (I) obtained into one of its salts.

More particularly, the reaction between compounds with formula (II) and (III) is carried out in an organic solvent such as a lower alcohol, for example: methanol, ethanol or isopropanol; dimethylsulfoxide (DMSO); a linear or cyclic ether; or an amide such as dimethylformamide (DMF) or dimethylacetamide; preferably using at least equimolecular quantities of reactants.

The reaction temperature is in the range from ambient temperature to the reflux temperature of the selected solvent.

When $R_1$ represents hydrogen, it is preferable to protect the functional group with a protector group to avoid undesirable condensation reactions and to facilitate the desired condensation reaction.

Regarding protective groups, it is possible to use the usual groups for protecting the hydroxyl group such as methoxyethoxymethyl (MEM) or benzyl, employing well known techniques.

In the same manner, the other sensitive groups that may be present (for example $R_7$=COOH) can be protected employing well known methods.

Compounds with formula (II) are compounds that are known in the literature, or they can be prepared using methods that are analogous to the methods described in the literature.

Compounds with formula (III) in which $R_4$ is a —$NR_5R_6$ group and X is $CH_2$, and their salts or solvates, are novel and constitute a further aspect of the present invention. Said compounds, with formula (III') given below, can be prepared in accordance with the following scheme 1:

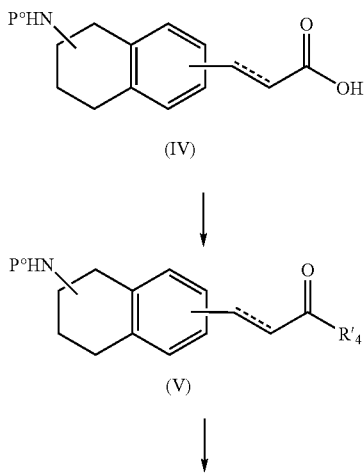

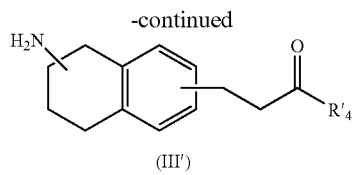

(III')

in which $R'_4$ is an —$NR_5R_6$ group, $NR_5R_6$ being as defined above, P° is a protective group and the dotted line represents a possible double bond.

Regarding protective groups P°, it is possible to use the usual groups for protecting amines, such as tert-butoxycarbonyl, acetyl or benzyloxycarbonyl.

These protective groups can be cleaved using the usual methods described for the selected protective group; in the case of tert-butoxycarbonyl, for example, cleavage is normally achieved by acid hydrolysis.

The activity of the compounds of the present invention as regards beta-3 activity has been demonstrated through in vitro tests on the human colon using the method described in EP-B-0 436 435 and by T. Croci et al., Br. J. Pharmacol., 1997, 122; 139P.

These surprising properties of compounds with formula (I) allow their use as drugs with a beta-3 agonist action to be envisaged.

Further, compounds with formula (I) have low toxicity; in particular, their acute toxicity is compatible with their use as drugs in treating disorders in which compounds having an affinity for the beta-3 receptor, in particular beta-3 agonists, are applicable. Such disorders have been described in the literature. Compounds with formula (I) and their pharmaceutically acceptable salts can thus, for example, be indicated in the treatment of gastro-intestinal diseases such as irritable bowel syndrome, as modulators for intestinal motricity, as lipolytics, as anti-obesity agents, as anti-diabetic agents, as psychotropic agents, as anti-glaucoma agents, as cicatrizing agents, as anti-depressants, as a uterine contraction inhibitor, as tocolytics to prevent or retard premature birth, or in the treatment and/or prophylaxis of dysmenorrhea. Further, compounds with formula (I) can be used in treating certain disorders of the central nervous system, such as depression, for example, and certain problems with the urinary system such as urinary incontinence.

The use of the compounds with formula (I) above, and that of their pharmaceutically acceptable salts and solvates, for the preparation of the drugs designated above, constitutes a further aspect of the present invention.

For such a use, an effective quantity of a compound with formula (I) or one of its pharmaceutically acceptable salts and solvates is administered to mammals in need of such a treatment.

The above compounds with formula (I) and their pharmaceutically acceptable salts and solvates can be used in daily doses of 0.01 to 20 mg per kg of body weight of the mammal to be treated, preferably in daily doses of 0.1 to 10 mg/kg. In humans, the dose is preferably 0.5 mg to 1500 mg per day, in particular 2.5 to 500 mg depending on the age of the subject to be treated, the type of treatment—prophylactic or curative—and the severity of the disease. Compounds with formula (I) are generally administered in a dosage of 0.1 to 500 mg, preferably 0.5 to 100 mg of active principle, once to five times a day.

Said dosages are preferably formulated in pharmaceutical compositions in which the active principle is mixed with a pharmaceutical excipient.

In a further aspect, then, the present invention concerns pharmaceutical compositions comprising, as the active principle, a compound with formula (I) above or one of its pharmaceutically acceptable salts and solvates.

In the pharmaceutical compositions of the present invention for oral, sublingual, subcutaneous, intramuscular, intravenous, topical, transdermal or rectal administration, the active ingredients with formula (I) above, their pharmaceutically acceptable salts and solvates, can be administered to animals and humans in unitary administration forms mixed with conventional pharmaceutical supports to treat the diseases cited above. Suitable unitary administration forms comprise oral administration forms such as tablets, gelatin capsules, powders, granules and oral solutions or suspensions, sublingual and buccal administration forms, subcutaneous, intramuscular or intravenous administration forms, local administration forms and rectal administration forms.

When preparing a solid composition in the form of tablets, the principal active ingredient is mixed with a pharmaceutical vehicle such as gelatine, starch, lactose, magnesium stearate, talc, gum Arabic or the like. Tablets can be coated with sugar or with other suitable materials, or they can be treated so that they have a prolonged or slow effect and they continuously release a predetermined quantity of active principle.

A gelatin capsule preparation is obtained by mixing the active ingredient with a diluent and pouring the mixture obtained into soft or hard gelatin capsules.

A preparation in the form of a syrup or elixir can contain the active ingredient along with a sweetener, preferably calorie-free, methylparaben and propylparaben as antiseptics, and a suitable taste producing agent and colorant.

Water-dispersible powders or granules can contain the active ingredient mixed with dispersion agents or wetting agents, or suspension agents such as polyvinylpyrrolidone, and again with sweeteners or taste correcting agents.

For local administration, the active principle is mixed with an excipient for preparing creams or unguents or it is dissolved in a vehicle for intraocular administration, for example in the form of an eye lotion.

For rectal administration, suppositories are used that are prepared with binders that melt at the temperature of the rectum, for example cocoa butter or polyethylene glycols.

For parenteral administration, aqueous suspensions, saline solutions or sterile injectable solutions are used that contain pharmacologically compatible dispersion agents and/or wetting agents, for example propylene glycol or butylene glycol.

The active principle can also be formulated in the form of microcapsules, optionally with one or more supports or additives.

In a further aspect, the present invention concerns a method for treating diseases that are improved by a beta-3 agonist action, which comprises administering a compound with formula (I) or one of its pharmaceutically acceptable salts or solvates.

Compounds with formula (I), in particular compounds (I) labeled with an isotope, can also be used as laboratory tools in biochemical tests.

Compounds with formula (I) bind to the beta-3 adrenergic receptor. Thus, said compounds can be used in an ordinary binding test in which an organic tissue in which this receptor is particularly abundant is used, and the quantity of compound (I) displaced by a test compound is measured to determine the affinity of said compound towards binding sites for that particular receptor.

A further specific subject matter of the present invention is thus a reagent that can be used in biochemical tests, which comprises at least one suitably labeled compound with formula (I).

The following examples better illustrate the invention.

PREPARATION 1

(2S)-2-amino-7-piperidinocarbonylmethoxy-tetralin hydrochloride monohydrate a) (2S)-2-tert-butoxycarbonylamino-7-piperidinocarbonylmethoxy-tetralin 8.1 g (0.025 mole) of (2S)-2-tert-butoxycarbonylamino-7-hydroxycarbonylmethoxy-tetralin, 2.5 ml (0.025 mole) of piperidine, 11 g (0.025 mole) of benzotriazol-1-yloxy-tris(dimethylamino)phosphonium hexafluorophosphate (BOP) and 5.3 ml of triethylamine in 250 ml of dimethylformamide were mixed at ambient temperature for 6 hours. The solvent was evaporated off, the residue was taken up in water, it was extracted with ethyl acetate, the organic phase was washed with a saturated $NaHCO_3$ solution, filtered over celite and washed with a dilute solution of acetic acid and with water. It was dried and the solvent was evaporated off under reduced pressure. The product was purified by crystallization from a 1:1 ethyl/hexane mixture. The product of the heading was obtained.

MP: 102–103° C.

b)
(2S)-2-amino-7-piperidinocarbonylmethoxy-tetralin hydrochloride monohydrate 2.9 g of the product from the previous step in 56 ml of ethyl acetate were cooled to +5° C. and 28 ml of a 3N solution of hydrochloric acid in ethyl acetate were added. It was stirred at ambient temperature for 24 hours. The compound of the heading was isolated in the form of a white solid by filtering.

PREPARATION 2

(2S)-2-amino-7-(n-butylaminocarbonylmethoxy)-tetralin hydrochloride a) (2S)-2-tert-butoxycarbonylamino-7-(n-butylaminocarbonylmethoxy)-tetralin 4 g (0.0013 mole) of (2S)-2-tert-butoxycarbonylamino-7-hydroxycarbonylmethoxy-tetralin and 1.66 g (0.0143 mole) of N-hydroxysuccinimide in 40 ml of acetonitrile were stirred at ambient temperature for 3 hours and 2.95 g (0.0143 mole) of DCC (dicyclohexylcarbodiimide) in 15 ml of ethyl ether were added. 1.3 ml (0.0195 mole) of n-butylamine were then added and it was stirred at ambient temperature overnight. The solvent was evaporated off, the residue was taken up in water; it was extracted with ethyl acetate. The organic phase was washed with an aqueous sodium bicarbonate solution, dried and the solvent was evaporated off under reduced pressure. The residue was taken up in a 1:1 ethyl acetate/hexane mixture; the precipitate formed was filtered off and oven dried. The product of the heading was obtained as a white solid.

MP: 127–129° C.

b) (2S)-2-amino-7-(n-butylaminocarbonylmethoxy)-tetralin hydrochloride

A mixture of 1.95 g (0.0054 mole) of the product from the previous step in 40 ml of ethyl acetate and 20 ml of methylene chloride was cooled to +5° C. and 20 ml of a 3N solution of hydrochloric acid in ethyl acetate were added. It was stirred at ambient temperature for 24 hours. The precipitate thus formed was filtered and crystallized from isopropanol. The product of the heading was obtained.

MP: 154–156° C.

PREPARATION 3

(2S)-2-amino-7-aminocarbonylmethoxy-tetralin hydrochloride a) (2S)-2-tert-butoxycarbonylamino-7-aminocarbonylmethoxy-tetralin 0.16 g of 60% NaH (0.004 mole) and 3.5 ml of anhydrous DMF were stirred at ambient temperature in a stream of nitrogen and 1 g (0.0038 mole) of (2S)-2-tert-butoxycarbonylamino-7-hydroxy-tetralin in 9 ml of anhydrous DMF and 0.52 g (0.0038 mole) of 2-bromoacetamide in 2.5 ml of anhydrous DMF were added. It was stirred at ambient temperature for 6 hours then the mixture was poured into water. The precipitated product was filtered and the product of the heading was then obtained.

b) (2S)-2-amino-7-aminocarbonylmethoxy-tetralin hydrochloride

A mixture of 4.25 g (0.013 mole) of the product from the preceding step in 100 ml of ethyl acetate and 40 ml of methanol was cooled to +5° C. and 53 ml of a 3N solution of hydrochloric acid in ethyl acetate was added. It was stirred at ambient temperature for 24 hours. The compound of the heading was isolated by filtering.

MP: >250° C.

PREPARATION 4

(2S)-2-amino-7-(N,N-diethylaminocarbonylmethoxy)-tetralin a) (2S)-2-tert-butoxycarbonylamino-7-(N,N-diethylaminocarbonylmethoxy)-tetralin 3 g (0.009 mole) of (2S)-2-tert-butoxycarbonylamino-7-hydroxycarbonylmethoxy-tetralin, 0.93 ml of N,N-diethylamine (0.009 mole), 4 g (0.009 mole) of BOP and 1.9 ml (0.0135 mole) of triethylamine in 90 ml of anhydrous DMF were stirred at ambient temperature for 6 hours. The solvent was evaporated off and the residue was taken up in ethyl acetate. It was washed with a sodium bicarbonate solution. An emulsion was obtained which was filtered over celite. The filtered solution was washed with acetic acid and then with water. The organic phase was dried over sodium sulfate and the solvent was evaporated off under reduced pressure. The product was purified by flash chromatography, eluting with a 1:1 ethyl acetate/hexane mixture. The product of the heading was obtained in the form of a very dense oil.

b) (2S)-2-amino-7-(N,N-diethylaminocarbonylmethoxy)-tetralin

A mixture of 2.6 g (0.007 mole) of the product from the preceding step in a mixture of 52 ml of ethyl acetate and 26 ml of methylene chloride was cooled to +5° C. and 26 ml of a 3N solution of hydrochloric acid in ethyl acetate were added. It was stirred at ambient temperature for 24 hours, the solvent was evaporated off under reduced pressure and the residue was taken up in water; the pH was made basic with $NH_4OH$ and it was extracted with ethyl acetate; the organic phase was dried and the solvent was evaporated off under reduced pressure. The crude product was purified by silica gel chromatography, eluting with a 9:1 methylene chloride/methanol mixture to obtain the product of the heading as an oil.

PREPARATION 5

(2S)-2-amino-7-benzylaminocarbonylmethoxy-tetralin hydrochloride a) (2S)-2-tert-butoxycarbonylamino-7-benzylaminocarbonylmethoxy-tetralin 2.26 g (7 mmole) of (2S)-2-tert-butoxycarbonylamino-7-hydroxycarbonylmethoxy-tetralin were mixed with 80 ml of DMF and 0.749 g (7 mmole) of benzylamine, 3.1 g of BOP and 1.47 ml (10.5 mmole) of triethylamine were added. The mixture was stirred at ambient temperature for 6 hours then left to stand overnight without stirring. The solvent was evaporated off; the residue was taken up in ethyl acetate and washed with a 5% sodium bicarbonate solution. The organic phase was dried and the solvent was evaporated off under reduced pressure. The compound of the heading was obtained.

MP: 135–137° C.

$[\alpha]_D$=−52.2° (conc. 1% in methanol).

b) (2S)-2-amino-7-benzylaminocarbonylmethoxy-tetralin hydrochloride 2.5 g of the product from the preceding step and 20 ml of ethyl acetate were mixed and 20 ml of an ethyl acetate solution saturated with hydrochloric acid were added. It was stirred at ambient temperature for 3 hours and the precipitate formed was then filtered. The product of the heading was obtained.

MP: 174–177° C.

$[\alpha]_D$=−36.7° (conc. 1% in methanol).

PREPARATION 6

(2S)-2-amino-7-(2-ethoxycarbonylethyl)-tetralin a) (2S)-2-benzyloxycarbonylamino-7-trifluoromethanesulfonate-tetralin 1 g (3.37 mmole) of (2S)-2-benzyloxycarbonylamino-7-hydroxy-tetralin was dissolved in anhydrous pyridine. It was cooled to 0° C. and then 0.600 ml (3.7 mmole) of triflic anhydride was added. It was stirred at ambient temperature for 4 hours and then poured into 20 ml of water. It was extracted with ethyl ether, the organic phase was dried over sodium sulfate and the solvent was evaporated off under reduced pressure. The crude product was purified by silica gel column chromatography, eluting with a 8:2 cyclohexane/ethyl acetate mixture. The product of the heading was obtained.

b) (2S)-2-benzyloxycarbonylamino-7-(3-ethoxy-3-oxo-1-propenyl)-tetralin 4.5 g (10.5 mmole) of the product from the preceding step, 2.25 ml of triethylamine and 1.36 g (13.65 mmole) of ethyl acetate were mixed and 194 mg (0.74 mmole) of triphenylphosphine were added. 83 mg of Pd(OAc)$_2$ was then added under a stream of nitrogen. The receptacle was sealed and after 5 hours at 90° C., another 41 mg of Pd(OAc)$_2$ and 97 mg of triphenylphosphine were added and it was stirred at 90° C. for 2 hours. The crude reaction product was purified by flash chromatography, eluting with a 8:2 hexane/ethyl acetate mixture. The product of the heading was obtained.

MP: 119–121° C.

$[\alpha]_D$=−59.2° (conc. 1% in methanol).

c) (2S)-2-amino-7-(2-ethoxycarbonylethyl)-tetralin 1.3 g (34.3 mmole) of the product from the preceding step were dissolved in 100 ml of ethanol and 130 mg of 10% Pd/C were added. It was hydrogenated for 4 hours at ambient temperature, the catalyst was filtered off and the solvent was evaporated off under reduced pressure. 660 mg of the product of the heading were obtained.

PREPARATION 7

(2S)-2-amino-7-[2-(piperidinocarbonyl)ethyl]-tetralin a) (2S)-2-benzyloxycarbonylamino-7-(3-hydroxy-3-oxo-1-propenyl)-tetralin 2 g (5.3 mmole) of (2S)-2-benzyloxycarbonylamino-7-(3-ethoxy-3-oxo-1-propenyl)-tetralin were dissolved in 20 ml of methanol and 30 ml of THF, and 5.3 ml of 1N NaOH were added. The solution was stirred overnight at ambient temperature. The solvent was evaporated off, the residue was taken up in water and washed with ethyl ether; the aqueous phase was acidified with 5% citric acid and then extracted with ethyl acetate. It was dried over sodium sulfate and the solvent was evaporated off. The product of the heading was obtained.

b) (2S)-2-benzyloxycarbonylamino-7-(3-oxo-3-piperidino-1-propenyl)-tetralin The compound of the heading was obtained by carrying out the procedure described in preparation 4a) but using piperidine instead of N,N-diethylamine and the product of the preceding step instead of (2S)-2-tert-butoxycarbonylamino-7-hydroxycarbonylmethoxy-tetralin.

c) (2S)-2-amino-7-[2-(piperidinocarbonyl)-ethyl]-tetralin 890 mg (2.2 mmole) of the product from the preceding step were dissolved in a 1:1 methanol/THF mixture and 90 mg of 10% Pd/C were added. It was hydrogenated for 4 hours, the catalyst was filtered off and the solvent was evaporated off under reduced pressure. 500 mg of the product of the heading were obtained.

PREPARATION 8

4-benzyloxy-3-(N-propanesulfonyl-N-tert-butoxycarbonylamino)-1-((2S)-2,3-epoxypropoxy)-benzene a) 4-benzyloxy-3-propanesulfonylamino-benzene acetate 5.0 g (0.00194 mole) of 3-amino-4-benzyloxybenzene were mixed with 150 ml of methylene chloride in a nitrogen atmosphere and 3.3 ml (0.0236 mole) of triethylamine and 2.74 ml (0.0236 mole) of 1-propanesulfonyl chloride were added. It was stirred overnight at ambient temperature. It was washed with water, the two phases were separated and the organic phase was dried over sodium sulfate; it was filtered and the solvent was evaporated off under reduced pressure. The residue was taken up in isopropyl ether and the precipitate was filtered. The compound of the heading was obtained.

MP: 135–137° C.

b) 4-benzyloxy-3-(N-propanesulfonyl-N-tert-butoxycarbonylamino)-benzene acetate 5.8 g (0.016 mole) of the product from the preceding step were mixed with 100 ml of methylene chloride, and 4.2 g (0.0192 mole) of di-tert-butylbicarbonate and 0.40 g (0.0032 mole) of 4-(N,N-dimethylamino)pyridine were added. It was stirred overnight at ambient temperature, the solvent was evaporated off and purification was carried out by silica-gel column chromatography, eluting with a 85:15 cyclohexane/ethyl acetate mixture. The compound of the heading was obtained.

MP: 83–85° C.

c) 4-benzyloxy-3-(N-propanesulfonyl-N-tert-butoxycarbonylamino)-phenol 5.4 g (0.0116 mole) of the product from the preceding step were mixed with 150 ml of methanol and 13.9 ml (0.0139 mole) of 1N NaOH were added. It was stirred at ambient temperature for 30 minutes then citric acid was added to a pH of 6, and the solvent was evaporated off. It was taken up in ethyl acetate, washed with water and the two phases were separated; the organic phase was dried over sodium sulfate and it was filtered, then the solvent was evaporated off under reduced pressure. The compound of the heading was obtained.

MP: 155–157° C.

d) 4-benzyloxy-3-(N-propanesulfonyl-N-tert-butoxycarbonylamino)-1-((2S)-2,3-epoxypropoxy)-benzene 4.3 g (0.0102 mole) of the product from the preceding step were mixed with 100 ml of acetone and 4.6 g of anhydrous grated potassium carbonate and 3.3 g (0.0125 mole) of (2S)(+)-glycidyl nosylate were added. It was heated under reflux for 20 hours, then filtered, the solvent was evaporated off and purification was carried out on a silica gel chromatographic column, eluting with a 75:25 cyclohexane/ethyl acetate mixture. The compound of the heading was obtained as a dense oil.

$[\alpha]_D$=+4.5° (conc. 1% in ethanol).

EXAMPLE 1

1-(3-methylsulfonylamino-4-hydroxyphenoxy)-3-(7-ethoxycarbonylmethoxy-tetralin-2-yl-amino)-2-propanol a) 1-(3-methylsulfonylamino-4-benzyloxyphenoxy)-3-(7-ethoxycarbonylmethoxy-tetralin-2-yl-amino)-2-propanol 1.36 g (0.0032 mole) of 3-N-methylsulfonylamino-N-tert-butoxycarbonylamino-4-benzyloxy-1-(2,3-epoxypropoxy)-benzene, 1.04 g (0.0042 mole) of 2-amino-7-ethoxycarbonylmethoxy-tetralin and 0.26 g of $LiClO_4$ in 48 ml of $CH_3CN$ were mixed at 40° C. for 24 hours. The solvent was evaporated off, the residue was taken up in 30 ml of ethyl acetate, 10 ml of methylene chloride and 20 ml of a 3N solution of hydrochloric acid in ethyl acetate and the mixture was stirred at 40° C. for 6 hours. The solvent was evaporated off, an $NH_4OH$ solution was added to produce a basic pH and it was extracted with ethyl acetate. It was dried, the solvent was evaporated off and purification was carried out on a silica gel chromatographic column, eluting with a 9:1 methylene chloride/methanol mixture. 1.54 g of the product of the heading were obtained.

b) 1-(3-methylsulfonylamino-4-hydroxyphenoxy)-3-(7-ethoxycarbonylmethoxy-tetralin-2-yl-amino)-2-propanol 0.93 g (0.0015 mole) of the product from the preceding step in 17 ml of ethanol and 17 ml of tetrahydrofuran was hydrogenated at 40° C. at ambient pressure with 0.115 g of 10% Pd/C. The catalyst was filtered off and the solvent was evaporated off. The product was purified by silica gel column flash chromatography, eluting with an 85:15 methylene chloride/methanol mixture. 0.39 g of the product of the heading was obtained.

EXAMPLE 2

1-(3-methylsulfonylamino-4-hydroxyphenoxy)-3-(7-ethoxycarbonylmethoxy-tetralin-(2S)-2-yl-amino)-(2S)-2-propanol hydrate a) 1-(3-methylsulfonylamino-4-benzyloxyphenoxy)-3-(7-ethoxycarbonylmethoxy-tetralin-(2S)-2-yl-amino)-(2S)-2-propanol The compound of the heading was obtained using the procedure described in example 1a), but employing optically active compounds, namely 3-N-methylsulfonylamino-N-tert-butoxycarbonylamino-4-benzyloxy-1-((2S)-2,3-epoxypropoxy)-benzene and (2S)-2-amino-7-ethoxycarbonylmethoxy-tetralin.

$[\alpha]_D = -30.6°$ (conc. 0.5% methanol)

b) 1-(3-methylsulfonylamino-4-hydroxyphenoxy)-3-(7-ethoxycarbonylmethoxy-tetralin-(2S)-2-yl-amino)-(2S)-2-propanol hydrate The product of the heading was obtained using the procedure described in example 1b), but starting from the product from the preceding step.

$[\alpha]_D = -40.9°$ (conc. 1% methanol)

$^1H$ NMR, 200 MHz ($CDCl_3$) 1.25 (3H) t (J=7 Hz); 1.45–1.83 (1H) m; 1.90–2.26 (1H) m; 2.35–3.28 (7H) m; 2.82 (3H) s; 3.57–3.96 (2H) m; 4.00–4.31 (1H) m; 4.21 (2H) q (J=7 Hz); 4.51 (2H) s; 6.25–7.07 (6H) m.

EXAMPLE 3

1-(3-methylsulfonylamino-4-hydroxyphenoxy)-3-(7-piperidinocarbonylmethoxy-tetralin-2-yl-amino)-2-propanol a) 1-(3-methylsulfonylamino-4-benzyloxyphenoxy)-3-(7-piperidinocarbonylmethoxy-tetralin-2-yl-amino)-2-propanol 2.34 g (0.0052 mole) of 3-(N-methylsulfonyl-N-tert-butoxycarbonylamino)-4-benzyloxy-1-(2,3-epoxypropoxy)-benzene, 71 ml of ethanol and 1.44 g (0.0052 mole) of 2-amino-7-piperidinocarbonylmethoxy-tetralin from preparation 1 (base, racemate) were heated under reflux for 8 hours. It was stirred at ambient temperature overnight and then it was heated again under reflux for a further 6 hours. The solvent was evaporated off, the residue was taken up in 40 ml of ethyl acetate and 32.1 ml of a 3N solution of hydrochloric acid in ethyl acetate were added. It was heated under reflux for 5 hours and evaporated under reduced pressure. It was taken up in water, $NH_4OH$ was added until the pH was basic, and it was extracted with ethyl acetate. It was dried, the solvent was evaporated off and the product was purified by silica gel column flash chromatography, eluting with a 9:1 methylene chloride/methanol mixture. 1.3 g of the product of the heading was obtained.

b) 1-(3-methylsulfonylamino-4-hydroxyphenoxy)-3-(7-piperidinocarbonylmethoxy-tetralin-2-yl-amino)-2-propanol The product of the heading was obtained using the procedure described in example 1b) but starting from the product from the preceding step.

EXAMPLE 4

1-(3-methylsulfonylamino-4-hydroxyphenoxy)-3-(7-piperidinocarbonylmethoxy-tetralin-(2S)-2-yl-amino)-(2S)-2-propanol The compound of the heading was obtained using the procedure described in example 3, but employing optically active compounds, namely 3-N-(methylsulfonyl-N-tert-butoxycarbonylamino)-4-benzyloxy-1-((2S)-2,3-epoxypropoxy)-benzene and (2S)-2-amino-7-piperidinocarbonylmethoxy-tetralin from preparation 1 (base).

$^1H$ NMR, 200 MHz ($CDCl_3 + D_3COD$) 1.37–1.81 (6H) m; 1.96–2.25 (1H) m; 2.50–3.09 (7H) m; 2.87 (3H) s; 3.37–3.57 (4H) m; 3.76–3.96 (2H) m; 4.01–4.18 (1H) m; 4.57 (2H) bs; 6.41–6.60 (2H) m; 6.66 (1H) dd ($J_1$=8 Hz, $J_2$=3 Hz); 6.74 (1H) d (J=9 Hz); 6.86–7.01 (2H) m.

EXAMPLE 5

1-(3-methylsulfonylamino-4-hydroxyphenoxy)-3-(7-aminocarbonylmethoxy-tetralin-(2S)-2-yl-amino)-(2S)-2-propanol The compound of the heading was obtained using the procedure described in example 3, but employing 3-(N-methylsulfonyl-N-tert-butoxycarbonylamino)-4-benzyloxy- 1-((2S)-2,3-epoxypropoxy)-benzene and (2S)-2-amino-7-aminocarbonylmethoxy-tetralin from preparation 3.

$^1$H NMR, 200 MHz (DMSO-d$_6$+D$_2$O) 1.60–1.89 (1H) m; 2.06–2.33 (1H) m; 2.57–3.00 (3H) m; 2.93 (3H) s; 3.00–3.32 (3H) m; 3.33–3.53 (1H) m; 3.89 (2H) bd (J=5 Hz); 4.04–4.25 (1H) m; 4.36 (2H) s; 6.59–6.71 (2H) m; 6.75 (1H) dd (J$_1$=8 Hz, J$_2$=3 Hz); 6.79–6.92 (2H) m; 7.02 (1H) d (J=9 Hz).

EXAMPLE 6

1-(3-methylsulfonylamino-4-hydroxyphenoxy)-3-[7-(N,N-diethylaminocarbonylmethoxy)-tetralin-(2S)-2-yl-amino]-(2S)-2-propanol The compound of the heading was obtained using the procedure described in example 3, but employing 3-(N-methylsulfonyl-N-tert-butoxycarbonylamino)-4-benzyloxy-1-((2S)-2,3-epoxypropoxy)-benzene and (2S)-2-amino-7-(N,N-diethylaminoaminocarbonylmethoxy)-tetralin from preparation 4.

$^1$H NMR, 200 MHz (DMSO-d$_6$+D$_2$O) 0.79–1.28 (6H) m; 1.36–1.69 (1H) m; 1.90–2.15 (1H) m; 2.37–3.10 (7H) m; 2.93 (3H) s; 3.12–3.42 (4H) m; 3.73–4.12 (3H) m; 4.64 (2H) bs; 6.39–6.73 (3H) m; 6.73–6.88 (2H) m; 6.95 (1H) d (J=8 Hz).

EXAMPLE 7

1-(3-methylsulfonylamino-4-hydroxyphenoxy)-3-[7-(n-butylaminocarbonylmethoxy)-tetralin-(2S)-2-yl-amino]-(2S)-2-propanol The compound of the heading was obtained using the procedure described in example 3, but employing 3-(N-methylsulfonyl-N-tert-butoxycarbonylamino)-4-benzyloxy-1-((2S)-2,3-epoxypropoxy)-benzene and (2S)-2-amino-7-(n-butylaminocarbonylmethoxy)-tetralin from preparation 2 (base).

$^1$H NMR, 200 MHz (CDCl$_3$+D$_3$COD) 1.22 (3H) t (J=7 Hz); 1.08–1.78 (4H) m; 1.89–2.19 (1H) m; 2.38–3.11 (7H) m; 2.84 (3H) s; 3.20–3.42 (2H) m; 3.50–3.76 (1H) m; 3.85 (2H) bs; 3.96–4.17 (1H) m; 4.36 (2H) bs; 6.36–6.58 (2H) m; 6.59–6.70 (1H) m; 6.70–6.86 (1H) m; 6.87–7.10 (2H) m.

EXAMPLE 8

1-(3-methylsulfonylamino-4-hydroxyphenoxy)-3-(7-benzylaminocarbonylmethoxy-tetralin-(2S)-2-yl-amino)-(2S)-2-propanol The compound of the heading was obtained using the procedure described in example 3, but employing 3-(N-methylsulfonyl-N-tert-butoxycarbonylamino)-4-benzyloxy-1-((2S)-2,3-epoxypropoxy)-benzene and (2S)-2-amino-7-(benzylaminocarbonylmethoxy)-tetralin from preparation 5 (base).

$^1$H NMR, 200 MHz (CDCl$_3$+D$_3$COD) 1.34–1.69 (1H) m; 1.81–2.17 (1H) m; 2.33–3.10 (7H) m; 2.77 (3H) s; 3.55–3.92 (2H) m; 3.92–4.20 (1H) m; 4.39 (2H) bs; 4.45 (2H) bs; 6.26–6.52 (2H) m; 6.52–6.66 (1H) m; 6.66–6.81 (1H) m; 6.81–7.02 (2H) m; 7.10–7.43 (5H) m.

EXAMPLE 9

1-(3-propylsulfonylamino-4-hydroxyphenoxy)-3-(7-ethoxycarbonylmethoxy-tetralin-(2S)-2-yl-amino)-(2S)-2-propanol The compound of the heading was obtained using the procedure described in example 3, but employing 4-benzyloxy-3-(N-propanesulfonyl-N-tert-butoxycarbonylamino)-1-((2S)-2,3-epoxypropoxy)-benzene from preparation 8 and (2S)-2-amino-7-ethoxycarbonylmethoxy-tetralin.

$^1$H NMR, 200 MHz (CDCl$_3$) 0.84 (3H) t (J=7 Hz); 1.25 (3H) t (J=7 Hz); 1.49–1.93 (3H) m; 1.94–22.8 (1H) m; 2.38–3.41 (9H) m; 3.47–4.01 (2H) m; 4.03–4.36 (1H) m; 4.21 (2H) q (J=7 Hz); 4.39 (2H) bs; 6.07–7.16 (6H) m.

EXAMPLE 10

1-(3-methylsulfonylamino-4-hydroxyphenoxy)-3-[7-(2-(piperidinocarbonyl)-ethyl)-tetralin-(2S)-2-yl-amino]-(2S)-2-propanol The compound of the heading was obtained using the procedure described in example 3, but employing 3-(N-methylsulfonyl-N-tert-butoxycarbonylamino)-4-benzyloxy-1-((2S)-2,3-epoxypropoxy)-benzene and (2S)-2-amino-7-[2-(piperidinocarbonyl)ethyl]-tetralin from preparation 7.

$^1$H NMR, 200 MHz (DMSO-d$_6$+D$_2$O) 1.26–1.45 (4H) m; 1.45–1.62 (2H) m; 1.62–1.89 (1H) m; 2.09–2.29 (1H) m; 2.34–2.60 (2H) m; 2.61–3.47 (13H) m; 2.93 (3H) s; 3.89 (2H) d (J=5 Hz); 4.05–4.23 (1H) m; 6.68 (1H) dd (J$_1$=9 Hz, J$_2$=3 Hz); 6.75–6.89 (2H) m; 6.89–7.14 (3H) m.

EXAMPLE 11

1-(3-methylsulfonylamino-4-hydroxyphenoxy)-3-[7-(2-(ethoxycarbonyl)-ethyl)-tetralin-(2S)-2-yl-amino]-(2S)-2-propanol The compound of the heading was obtained using the procedure described in example 3, but employing 3-(N-methylsulfonyl-N-tert-butoxycarbonylamino)-4-benzyloxy-1-((2S)-2,3-epoxypropoxy)-benzene and (2S)-2-amino-7-[2-(ethoxycarbonyl)ethyl]-tetralin from preparation 6.

$^1$H NMR, 200 MHz (CDCl$_3$) 1.22 (3H) t (J=7 Hz); 1.48–1.71 (1H) m; 1.90–1.22 (1H) m; 2.42–3.21 (11H) m; 2.88 (3H) s; 3.86 (2H) bd; 3.97–4.26 (1H) m; 4.11 (2H) q (J=7 Hz); 6.47 (1H) dd (J$_1$=9 Hz, J$_2$=3 Hz); 6.73 (1H) d (J=9 Hz); 6.81–7.14 (4H) m.

EXAMPLE 12

1-(3-methylsulfonylamino-4-benzyloxyphenoxy)-3-(7-hydroxycarbonylmethoxy-tetralin-(2S)-2-yl-amino)-(2S)-2-propanol trifluoroacetate A solution of 0.240 g (0.47 mmole) of the product from example 2 was stirred for 1 hour in a mixture of 1.5 ml of methanol and 1.5 ml of an aqueous 1N sodium hydroxide solution. The reaction medium was then acidified by adding DOWEX (50 WX2) resin. The resin was washed 3 times in succession with water and 3 times with methanol. A 2N ammoniacal solution (15 ml) in methanol was added to the resin, and the heterogeneous medium was stirred for 15 min. The resin was filtered off, washed twice with methanol then stirring was recommenced for 15 min with 15 ml of a 2N ammoniacal solution. After filtering and washing the resin with methanol, the filtrates were combined and the solvent was evaporated off under reduced pressure. The product of the heading was obtained (0.05 g) after purification on preparative HPLC/MS and evaporating off the solvents.

HPLC/MS Operating Procedure

Apparatus: Two Shimatzu LC8 pumps coupled to an API 100 PE sciex mass spectrometer. A SCL-10A controller. A Gilson 215 injector-fraction collector.

Stationary phase: Xterra MS C18, 50×30 mm, 5 microm.

Mobile phase: Eluent A: $H_2O$/MeOH 95/5+$CF_3COOH$ 0.05%

Eluent B: $H_2O$/MeOH 5/95+$CF_3COOH$ 0.05%

Flow rate: 30 ml/min

Elution gradient:

| t (min) | % A | % B |
|---|---|---|
| 0 | 90 | 10 |
| 3 | 90 | 10 |
| 15 | 10 | 90 |
| 17 | 10 | 90 |

RT=7.48 min; [M+H$^+$]=481.4.

The purified product was analyzed by HPLC under the following conditions:

Apparatus: Two Shimatzu LC8 pumps coupled to a UV SPD10-A detector and to an API 100 PE sciex spectrometer. A SCL-10A controller. A Gilson 215 injector-fraction collector.

Stationary phase: Xterra MS C18, 50×4.6 mm, 5 microm.

Mobile phase: Eluent A: $H_2O$/MeOH 95/5+$CF_3COOH$ 0.05%

Eluent B: $H_2O$/MeOH 5/95+$CF_3COOH$ 0.05%

Flow rate: 3 ml/min

Elution gradient:

| t (min) | % A | % B |
|---|---|---|
| 0 | 90 | 10 |
| 1 | 90 | 10 |
| 9 | 10 | 90 |
| 10 | 10 | 90 |

RT=4.27 min; [M+H$^+$]=481.4.

The invention claimed is:

1. A compound of formula (I):

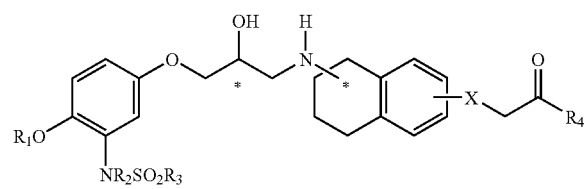

(I)

in which:
R$_1$ and R$_2$ are independently a hydrogen atom, a benzyl group, a benzoyl group, a —CO(C$_1$–C$_4$)Alk group, a —CH$_2$OCH$_3$ group, a —COO(C$_1$–C$_4$)Alk group or a benzyloxycarbonyl group; or R$_1$ and R$_2$ together form a carbonyl, methylene or di(C$_1$–C$_4$)Alk-methylene group so that R$_1$ and R$_2$ taken together with the oxygen and nitrogen atoms to which they are attached and the carbon atoms of the phenyl moiety to which the O and N atoms are attached form heterocyclyl;

R$_3$ is a hydrogen atom or a (C$_1$–C$_4$)Alk group;

R$_4$ is a hydroxyl group, a (C$_1$–C$_4$)alkoxy group or an —NR$_5$R$_6$ group;

R$_5$ and R$_6$ are independently a hydrogen atom; a (C$_1$–C$_4$) Alk group; an aryl or heteroaryl group, each of which is optionally substituted with an R$_7$ group; an aralkyl or heteroaralkyl group, each of which is optionally substituted with an R$_7$ group; or R$_5$ and R$_6$ taken together with the nitrogen atom to which they are attached form a saturated or unsaturated 5 to 7 atom cycle;

R$_7$ is a hydrogen atom, a halogen atom, a hydroxyl group, a (C$_1$–C$_4$)Alk group, a (C$_1$–C$_4$)alkoxy group, a —COOH group, a —COO(C$_1$–C$_4$)Alk group, a —CN group, an —NH(C$_1$–C$_4$)Alk group or an —N(C$_1$–C$_4$) Alk$_2$ group; and X is O or CH$_2$;

or a salt or solvate thereof.

2. The compound as claimed in claim 1, in which the tetralin is attached to the amino group at the beta position.

3. The compounds as claimed in claim 2, in which the two asymmetric carbon atoms marked with an asterisk "*" have the (S) configuration.

4. The compounds as claimed in claim 3, in which R$_5$ and R$_6$ taken together with the nitrogen atom to which they are attached form a piperidino, pyrrolidino, morpholino or thiomorpholino group.

5. The compounds as claimed in claim 4, in which the substituent —X—CH$_2$—CO—R$_4$ is connected to the 7 position of the tetralin.

6. The compounds as claimed in claim 5, in which R$_5$ is a hydrogen atom and R$_6$ is an aryl or heteroaryl group selected from phenyl, naphthyl and pyridyl.

7. The compounds as claimed in claim 5, in which R$_5$ is a hydrogen atom and R$_6$ is an aralkyl or heteroaralkyl group selected from benzyl, naphthylmethyl and pyridylmethyl.

8. The compound as claimed in claim 1, selected from:
1-3-methylsulfonylamino-4-hydroxyphenoxy)-3(7-ethoxycarbonylmethoxy-tetralin-2-yl-amino)-2-propanol;
1-(3-methylsulfonylamino-4-hydroxyphenoxy)-3-(7-ethoxycarbonylmethoxy-tetralin-(2S)-2-yl-amino)-(2S)-2-propanol;
1-(3-methylsulfonylamino-4-hydroxyphenoxy)-3-(7-piperidinocarbonylmethoxy-tetralin-2-yl-amino)-2-propanol;
1-(3-methylsulfonylamino-4-hydroxyphenoxy)-3-(7-piperidinocarbonylmethoxy-tetralin-(2S)-2-yl-amino)-(2S)-2-propanol;
1-(3-methylsulfonylamino-4-hydroxyphenoxy)-3-(7-aminocarbonylmethoxy-tetralin-(2S)-2-yl-amino)-(2S)-2-propanol;
1-(3-methylsulfonylamino-4-hydroxyphenoxy)-3-[7-(N, N-diethylaminocarbonylmethoxy)-tetralin-(2S)-2-yl-amino]-(2S)-2-propanol;

1-(3-methylsulfonylamino-4-hydroxyphenoxy)-3-[7-(n-butylaminocarbonylmethoxy)-tetralin-(2S)-2-yl-amino]-(2S)-2-propanol;

1-(3-methylsulfonylamino-4-hydroxyphenoxy)-3-(7-benzylaminocarbonylmethoxy-tetralin-(2S)-2-yl-amino)-(2S)-2-propanol;

1-(3-propylsulfonylamino-4-hydroxyphenoxy)-3-(7-ethoxycarbonylmethoxy-tetralin-(2S)-2-yl-amino)-(2S)-2-propanol;

1-(3-methylsulfonylamino-4-hydroxyphenoxy)-3-[7-(2-(piperidinocarbonyl)-ethyl)-tetralin-(2S)-2-yl-amino]-(2S)-2-propanol;

1-(3-methylsulfonylamino-4-hydroxyphenoxy)-3-[7-(2-(ethoxycarbonyl)-ethyl)-tetralin-(2S)-2-yl-amino)-(2S)-2-propanol;

1-(3-methylsulfonylamino-4-benzyloxyphenoxy)-3-(7-hydroxycarbonylmethoxy-tetralin-(2S)-2-yl-amino)-(2S)-2-propanol;

or a salt or solvate thereof.

9. A process for preparing a compound of formula (I) according to claim 1 comprising reacting a compound of formula (II):

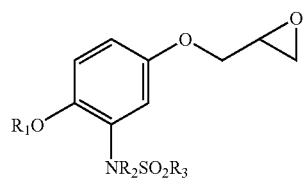

(II)

in which $R_1$, $R_2$ and $R_3$ are as defined in claim 1, with an amine of formula (III):

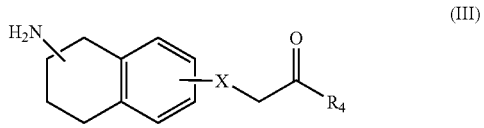

(III)

in which X and $R_4$ are as defined in claim 1 to form the compound of formula (I) corresponding thereto.

10. A pharmaceutical composition comprising a therapeutically effective amount of the compound of formula (I) as claimed in claim 1 or a pharmaceutically acceptable salt or solvate thereof, and a pharmaceutical excipient.

11. A pharmaceutical composition comprising a therapeutically effective amount of the compound of fornmla (I) as claimed in claim 2 or a pharmaceutically acceptable salt or solvate thereof, and a pharmaceutical excipient.

12. A pharmaceutical composition comprising a therapeutically effective amount of the compound of formula (I) as claimed in claim 3 or a pharmaceutically acceptable salt or solvate thereof, and a pharmaceutical excipient.

13. A pharmaceutical composition comprising a therapeutically effective amount of the compound of formula (I) as claimed in claim 4 or a pharmaceutically acceptable salt or solvate thereof, and a pharmaceutical excipient.

14. A pharmaceutical composition comprising a therapeutically effective amount of the compound of formula (I) as claimed in claim 5 or a pharmaceutically acceptable salt or solvate thereof, and a pharmaceutical excipient.

15. A pharmaceutical composition comprising a therapeutically effective amount of the compound of formula (I) as claimed in claim 6 or a pharmaceutically acceptable salt or solvate thereof, and a pharmaceutical excipient.

16. A pharmaceutical composition comprising a therapeutically effective amount of the compound of formula (I) as claimed in claim 7 or a pharmaceutically acceptable salt or solvate thereof, and a pharmaceutical exipient.

17. A pharmaceutical composition comprising a therapeutically effective amount of the compound of formula (I) as claimed in claim 8 or a pharmaceutically acceptable salt or solvate thereof, and a pharmaceutical excipient.

18. A method for treating urniary incontinence, in a patient in need thereof, comprising administering to the patient a therapeutically effective amount of the compound according to claim 1 or a pharmaceutically acceptable salt or solvate thereof.

19. A method for treating irritable bowel syndrome, in a petient in need thereof, comprising administering to the patient a therapeutically effective amount of the compound according to claim 1 or a pharmaceutically acceptable salt or solvate thereof.

20. A method for treating depression, in a patient in need thereof, comprising administering to the patient a therapeutically effective amount of the compound according to claim 1 or a pharmaceutically acceptable salt or solvate thereof.

* * * * *